(12) United States Patent
Wenzel et al.

(10) Patent No.: US 7,879,392 B2
(45) Date of Patent: Feb. 1, 2011

(54) COMPOSITIONS WITH ELONGATED PARTICLES HAVING VARYING CHARGES AND ASPECT RATIOS

(75) Inventors: Scott W. Wenzel, Neenah, WI (US); Stacy A. Mundschau, Weyauwega, WI (US); David William Koenig, Menasha, WI (US); Joe R. Feldkamp, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 459 days.

(21) Appl. No.: 11/872,114

(22) Filed: Oct. 15, 2007

(65) Prior Publication Data

US 2009/0098367 A1 Apr. 16, 2009

(51) Int. Cl.
*B05D 1/12* (2006.01)
(52) U.S. Cl. .................. 427/201; 427/180; 427/475
(58) Field of Classification Search .......... 427/180, 427/201, 475
See application file for complete search history.

(56) References Cited

U.S. PATENT DOCUMENTS

| 5,221,497 | A | 6/1993 | Watanabe et al. |
|---|---|---|---|
| 5,597,512 | A | 1/1997 | Watanabe et al. |
| 5,997,887 | A | 12/1999 | Ha et al. |
| 6,131,415 | A | 10/2000 | Chang et al. |
| 6,146,685 | A * | 11/2000 | Chrai et al. ............ 427/2.14 |
| 6,214,141 | B1 * | 4/2001 | Kim et al. ............... 156/72 |
| 6,494,974 | B2 | 12/2002 | Riddell |
| 7,030,176 | B2 | 4/2006 | Nohr et al. |
| 7,098,189 | B2 | 8/2006 | Malik |
| 2003/0228334 | A1 | 12/2003 | Mercier et al. |
| 2004/0123778 | A1 * | 7/2004 | Bagala, Sr. ............. 106/415 |
| 2006/0058210 | A1 | 3/2006 | Marsh et al. |

FOREIGN PATENT DOCUMENTS

JP 07-118008 5/1995

OTHER PUBLICATIONS

International Search Report of PCT/IB2008/052930—3 pages.
"Growth of Dumbbell-like ZnO Microcrystals Under Mild Conditions and Their Photoluminescence Properties", Inorganic Chemistry, vol. 46, No. 15, 2007, pp. 6204-6210.

* cited by examiner

*Primary Examiner*—Frederick J Parker
(74) *Attorney, Agent, or Firm*—Dority & Manning, P.A.

(57) ABSTRACT

The present disclosure is generally directed to a composition comprising one or more elongated particles having a diameter of from about 5 nm to about 500 nm, a length that is greater than the diameter and an aspect ratio of greater than about 1. The aspect ratio affects the orientation of such elongated particles in relation to a surface on which the composition is applied.

11 Claims, 6 Drawing Sheets

COMPOSITIONS WITH ELONGATED PARTICLES HAVING VARYING CHARGES AND ASPECT RATIOS

BACKGROUND

Particulates have been used for some time to improve the properties of various compositions. For example, particles have been utilized in compositions to absorb moisture, modify aesthetics, provide finishes to skin or surfaces, act as delivery vehicles, provide physical abrasion or other sensory properties to compositions, and aid in cleaning. Particles come in a wide variety of shapes and sizes, including nanometer and larger.

Particle size can affect the final look, feel, and functionality of each particle as well as that of the composition in which particles are present. For instance, smaller particles can affect the feel of a composition while larger particles can affect the look of a composition. As a result, a combination of different sized particles is often used in compositions so as to impart the benefits of each respective type of particle in the composition. However, it would improve efficiencies if one type of particle could be utilized to achieve the benefits of compositions with different sized particles. Additionally, modifications to particles affecting particle orientation in relation to other particles as well as surfaces would lead to unique sensory attributes which would also be desirable.

As such, a need exists for particles which would allow for one type of particle to be added to a composition to modify desired attributes of such a composition. In addition, a need exists for particles with varying charges and aspect ratios that can affect particle orientation.

SUMMARY

The present disclosure is directed to a composition having elongated particles. In this regard, the present disclosure is directed to elongated particles having varying charges and aspect ratios. Objects and advantages of the disclosure will be set forth in part in the following description, or may be obvious from the description, or may be learned through the practice of the disclosure.

The present disclosure is generally directed to a composition comprising one or more elongated particles having a diameter of from about 5 nm to about 500 nm, a length that is greater than the diameter and an aspect ratio of greater than about 1. The aspect ratio affects the orientation of such elongated particles in relation to a surface on which the composition is applied.

Other features and aspects of the present disclosure are discussed in greater detail below.

BRIEF DESCRIPTION OF THE DRAWINGS

A full and enabling disclosure of the present disclosure, including the best mode thereof to one of ordinary skill in the art, is set forth more particularly in the specification, including reference to the accompanying Figures in which.

DETAILED DESCRIPTION

It is to be understood by one of ordinary skill in the art that the present discussion is a description of exemplary embodiments only, and is not intended as limiting the broader aspects of the present disclosure, which broader aspects are embodied in the exemplary construction.

The present disclosure is generally directed to compositions having a plurality of elongated particles having varying charges and aspect ratios. By "particle," "particles," "particulate," "particulates" and the like, it is meant that the particulate material is generally in the form of discrete units. It has been discovered that varying charges and/or aspect ratios of an elongated particle can affect the orientation of such a particle in relation to other elongated particles in a composition. The elongated particles described herein allow for use of a single type of particle to achieve attributes that, in the past, a combination of particles would have been required to achieve.

For example, spherical particles having a diameter of less than 20 nanometers (nm) have been used in compositions because they provide a smooth feel. However, such particles lack the visibility found in larger particles. In contrast, larger particles having a length of greater than 90 nm can result in a rougher feel, but have the advantage that they are visible on a surface.

The elongated particles described herein allow for one type of particle that can modify both feel and visibility in a composition. In that regard, it has been determined that the charge of elongated particles can be varied along the length of such a particle and/or along the diameter of such a particle. For example, in certain embodiments, an elongated particle can have a first portion along the length of the elongated particle that has a first charge and a second portion along the length of the elongated particle that has a second charge. In certain embodiments, an elongated particle can have a first portion along the diameter of the elongated particle that has a first charge and a second portion along the diameter of the elongated particle that has a second charge.

Figure 1:
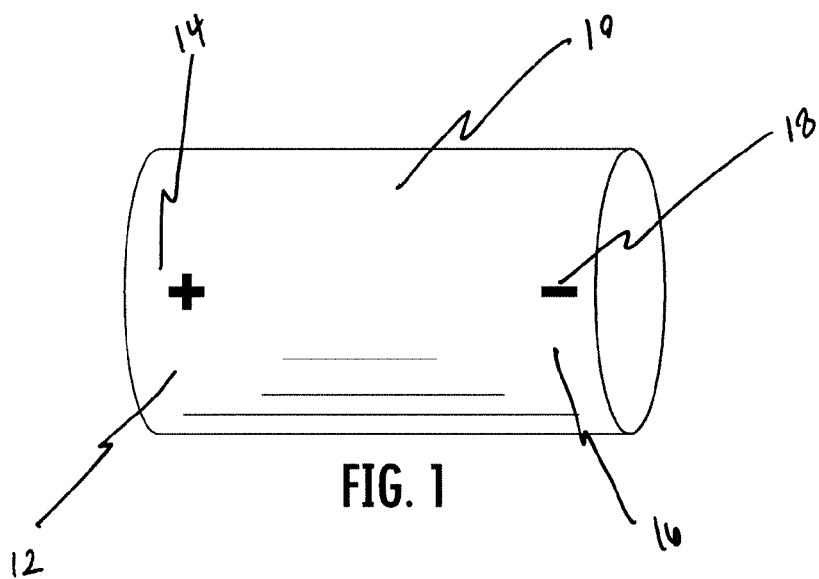
FIGS. 1-3 show elongated particles with varying charges in accordance with certain embodiments of the present disclosure.
Figure 2:
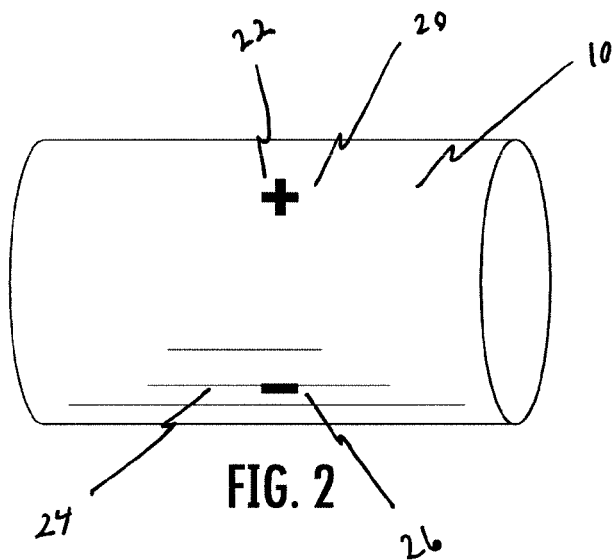
Figure 3:
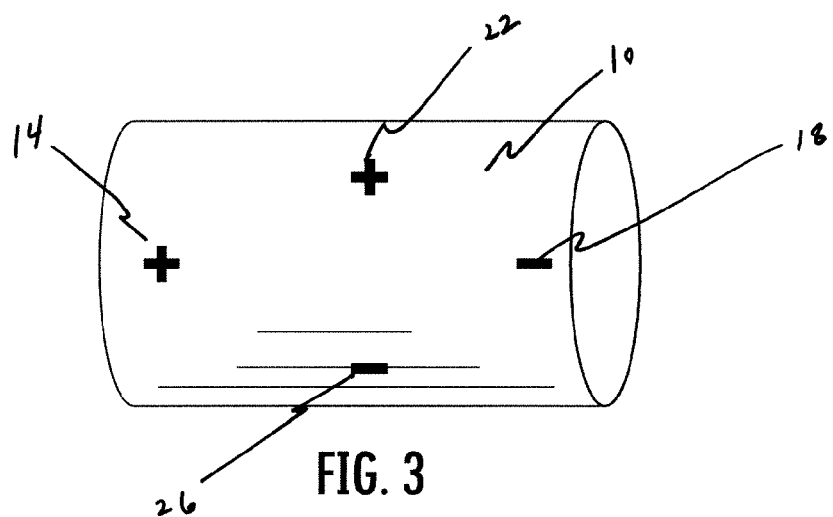

Referring to FIG. 1, in certain embodiments, a first portion 12 along the length of an elongated particle 10 has a positive charge 14 and a second portion 16 along the length has a negative charge 18. In some embodiments, as depicted in FIG. 2, a first portion 20 along the diameter of an elongated particle 10 has a positive charge 22 and a second portion 24 along the diameter has a negative charge 26. As shown in FIG. 3, in certain embodiments a first portion 12 along the length of an elongated particle 10 has a positive charge 14, a second portion 16 along the length has a negative charge 18, a first portion 20 along the diameter has a positive charge 22, and a second portion 24 along the diameter has a negative charge 26.

Figure 4:
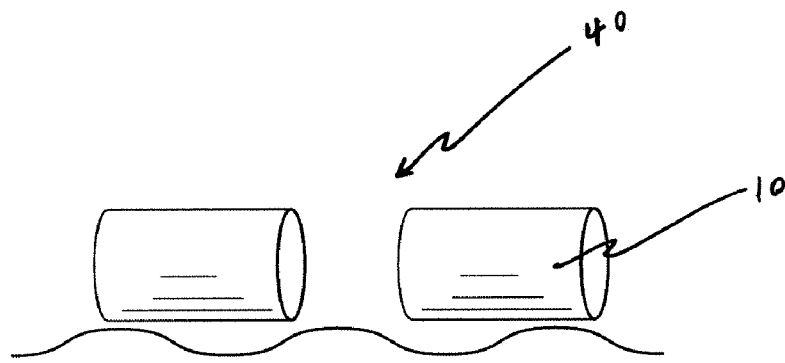
FIGS. 4-9 show different orientations of particles in accordance with certain embodiments of the present disclosure.
Figure 5:
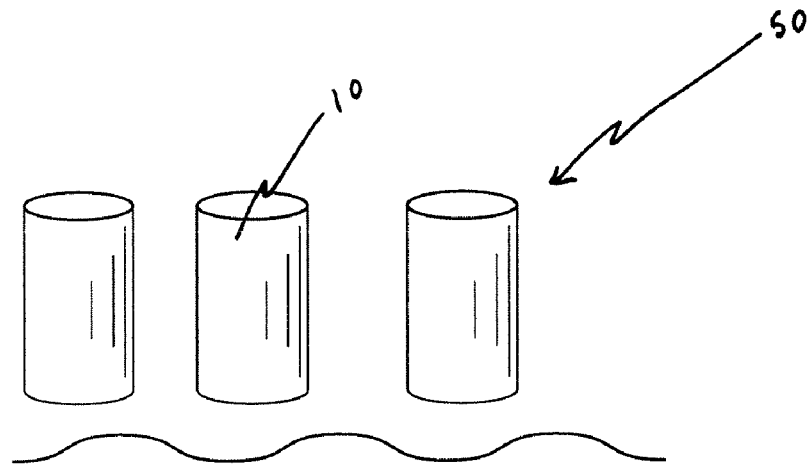
Figure 6:
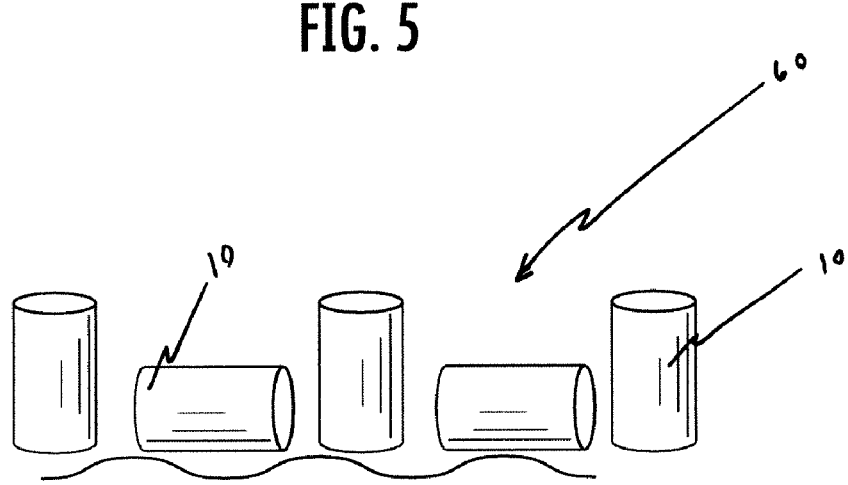

Referring to FIGS. 4-6, one of the advantages of the elongated particles of the present disclosure includes the capability to alter feel and visibility of a composition by utilizing varying charges in such particles.

Referring to FIG. 4, if the elongated particles 10 of the present disclosure are oriented flat on a surface such that they are generally horizontally adjacent to one another 40, the composition can have a smooth feel. Conversely, if the elongated particles of the present disclosure are positioned such that they are vertically adjacent to one another 50 as shown in FIG. 5, the composition can have a rough feel. If the elongated particles are positioned with horizontal particles adjacent to vertical particles 60, as illustrated in FIG. 6, the composition would have a combination of feel. It should be appreciated that any combination of the above-described orientations is contemplated by the present disclosure. For example, one could go from rough to smooth or from smooth to rough as the elongated particles changed orientation.

Figure 7:
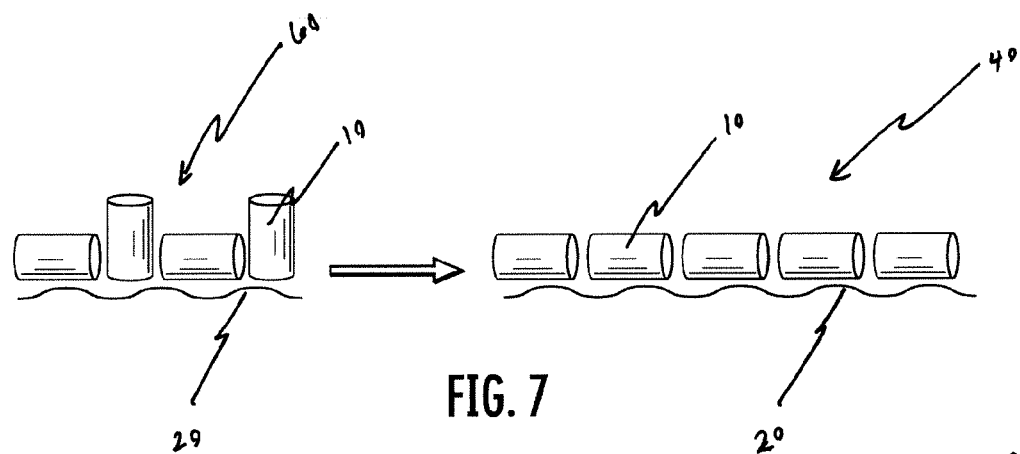
Figure 8:
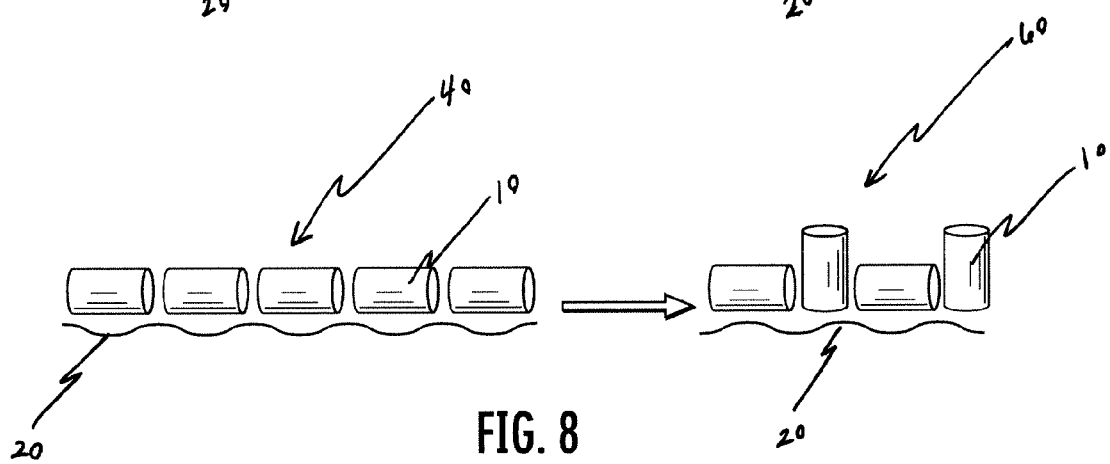

In certain embodiments of the present disclosure, a user applying the composition will lead to the elongated particles changing orientation. For instance, referring to FIG. 7, the elongated particles are oriented with horizontal particles adjacent to vertical particles 60 prior to being rubbed by a user, upon which, the particles are oriented horizontally adjacent to one another 40. Similarly, referring to FIG. 8, the elongated particles are oriented horizontally adjacent to one another 40 prior to be rubbed by a user upon which, the particles are oriented with horizontal particles adjacent to vertical particles 60.

Figure 9:
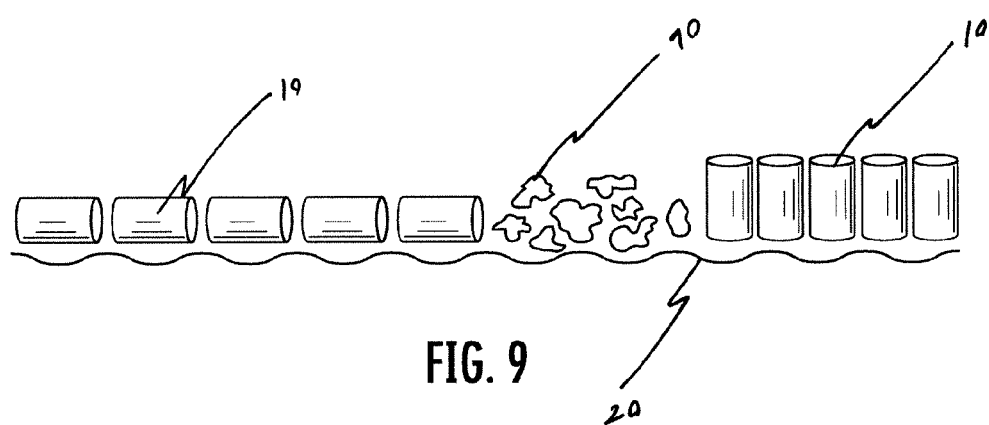

In addition, the composition can optionally include additional particles that can have any desired shape so as to allow for unique sensory attributes in accordance with the present disclosure. For example, referring to FIG. 9, amorphous particles 90 are positioned on a surface 20 between elongated particles 10 of the present disclosure allowing for unique sensory attributes.

It has also been discovered that certain aspect ratios of elongated particles result in a much greater adhesive force between elongated particles and a surface. The aspect ratios described herein allow for use of a single type of particle to achieve attributes that, in the past, a combination of particles would have been required to achieve.

In that regard, it has been discovered through a study of van der Waals forces that the aspect ratio of an elongated particle can affect adhesive force.

The van der Waals force, which is generally attractive in nature, is a short range force and decays rapidly to zero away from a surface. The origin of the van der Waals force lies in the instantaneous dipole generated by the fluctuation of electron cloud surrounding the nucleus of electrically neutral atoms.

The van der Waals force for a sphere near a surface is given by:

$$F_s = \frac{A_{132}d}{12z_0^2}$$

Where $A_{132}$ is the Hamaker constant for substances "1" and "2" in presence of medium "3," and $z_0$ is the separation distance.

The van der Waals force for a cylinder, oriented parallel, interacting with a surface is given by:

$$F_{cyl}^{//} = \frac{A_{132}lD^{1/2}}{16z_0^{5/2}}$$

The diameter notation is changed to distinguish the sphere diameter, d, from the cylinder diameter, D. Cylinder length is given by l.

If the cylinder is instead perpendicular to the flat surface, then the interaction force is given by:

$$F_{cyl}^{\perp} = A\frac{D^2}{24z_0^3}$$

An aspect ratio for the cylinder is defined as the cylinder length, divided by the cylinder diameter:

$$\alpha = \frac{l}{D}$$

The adhesive forces for a sphere and cylinder are compared under the constraint that the volume of each particle is the same:

$$\frac{4}{3}\pi\left(\frac{d}{2}\right)^3 = \pi\left(\frac{D}{2}\right)^2 l$$

Combining the equations, the ratio of $F_{cyl}^{//}/F_{sph}$ is:

$$\frac{F_{cyl}^{//}}{F_{sph}} = \left(\frac{9}{32}\right)^{1/3}\alpha^{2/3}\sqrt{\frac{D}{z_0}}$$

The ratio of $F_{cyl}^{//}/F_{cyl}^{\perp}$ is:

$$\frac{F_{cyl}^{//}}{F_{cyl}^{\perp}} = 1.5\alpha\sqrt{\frac{z_0}{D}}$$

The calculations assume that all materials are the same, which is appropriate when considering geometrical effects. For a nanoparticle, the separation distance $z_0$, can be taken to be about 1 nm, which is regulated by the interplay between attractive and repulsive forces.

Based on the above formulas, it has been determined that if the aspect ratio is assumed to be about 5, then the cylinder diameter has only to be above 1 nm to experience twice the adhesive force as the sphere. Maintaining the same aspect ratio, a cylinder diameter of 100 nm would experience an attachment force of approximately twenty times greater than that for a sphere. As such, it has been determined that an elongated particle positioned parallel to a surface is far more likely to remain attached to such a surface than a spherical particle.

Figure 10:
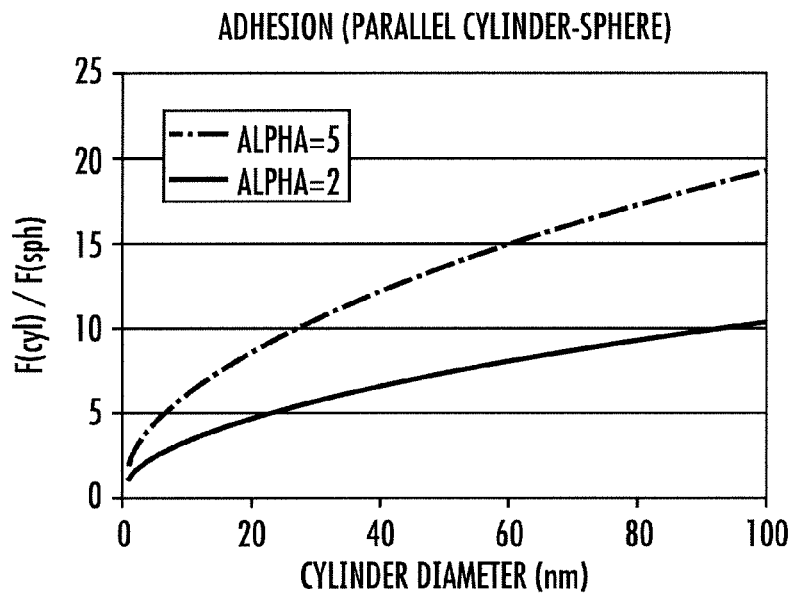
FIG. 10 shows a graph comparing a sphere and a parallel cylinder at aspect ratios of 2 and 5.
Figure 11:
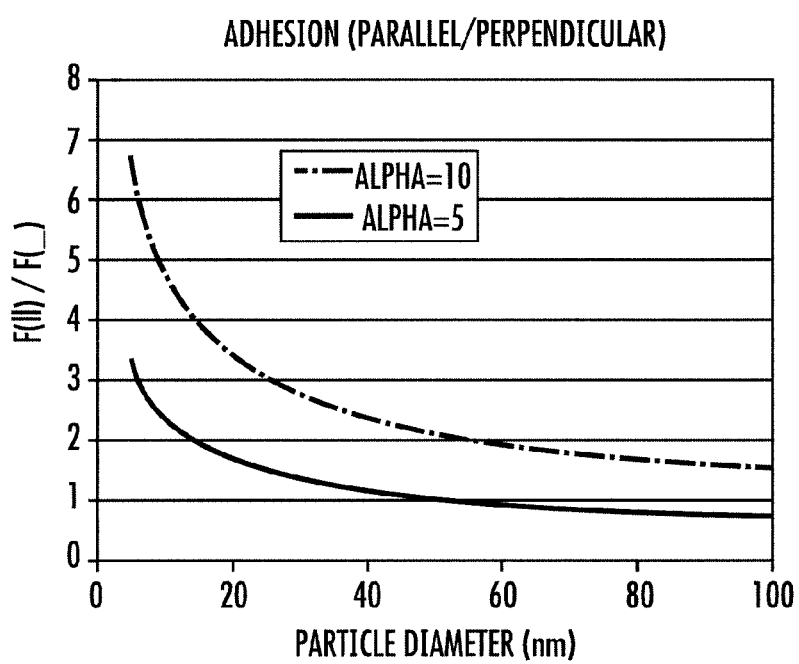
FIG. 11 shows a graph comparing cylinders in the parallel and perpendicular orientations at aspect ratios of 5 and 10.

Referring to FIG. 10, results are graphed comparing a parallel cylinder and a sphere at aspect ratios of 5 and 2. Additionally, referring to FIG. 11, results are graphed comparing cylinders in the parallel and perpendicular orientations at aspect ratios of 5 and 10.

Without intending to be limited by theory, such results suggest that if elongated particles are oriented flat in relation to a surface, they have improved adhesion in comparison to elongated particles that are oriented perpendicular to a surface, or a sphere of equal volume. This high level of adherence, in combination with the inherent oil or water absorbing characteristics of the particle, can impart a protective layer of particles over the skin. The particles can effectively absorb or otherwise prevent the skin from contacting irritating substances such as those found in urine and feces. Greater adherence of these particles would allow for greater protection than what is provided by traditional skin protectant powders such as talc. An additional benefit provided by the greater level of adherence includes but is not limited to sustained skin or hair conditioning.

Figure 12:
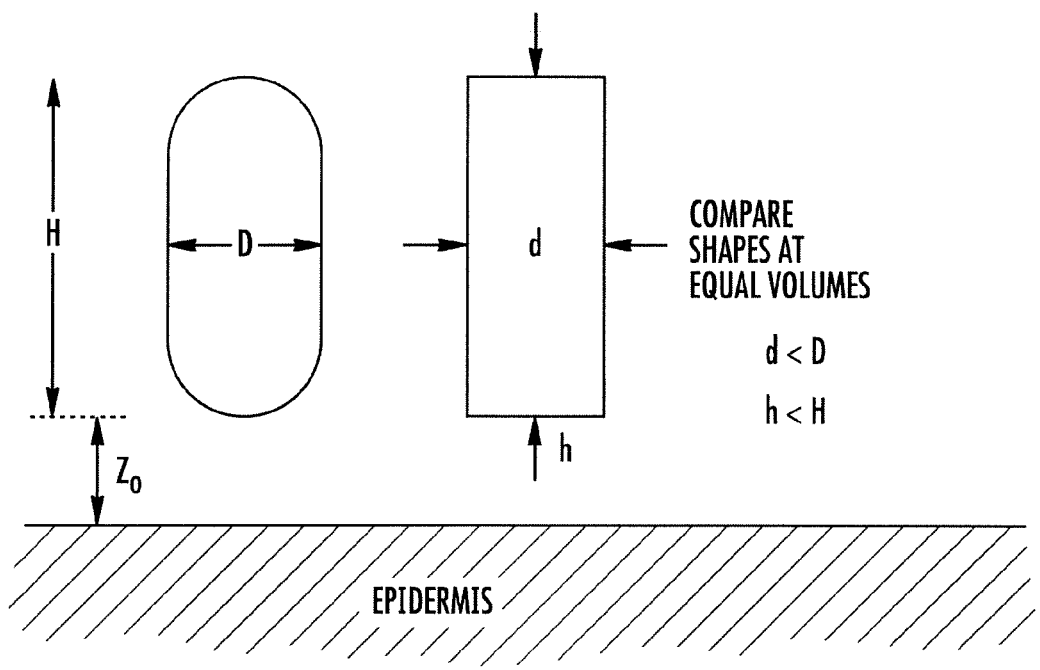
FIG. 12 show sausage shaped and cylindrically shaped elongated particles in accordance with certain embodiments of the present disclosure.

There are potentially many kinds of elongated particles, so to highlight features that are peculiar to elongated particles having a right-circular-cylinder form, the following discussion is directed to sausage shaped and cylindrically shaped rod shaped particles. Such elongated particles are depicted in FIG. 12.

Computation of the adhesive van der Waals force for these two rod-shaped particles, when oriented perpendicular to the surface at equal distances from the surface and equal volumes, leads to interesting findings. First, the attachment force for a cylinder exceeds that of a sausage shaped particle for essentially all aspect ratios and particle diameters, when compared in the perpendicular, or erect state. Second, the adhesive force for the cylinder in the perpendicular orientation is the same as that in the parallel orientation at a critical, or threshold, diameter.

A review of an equation described above supports this finding. As described above, the ratio of $F_{cyl}^{//}/F_{cyl}^{\perp}$ is:

$$\frac{F_{cyl}^{//}}{F_{cyl}^{\perp}} = 1.5\alpha\sqrt{\frac{z_0}{D}}$$

The left side is the ratio of the two forces in the two orientations. Setting this to unity, one can readily solve for the diameter D, as a function of aspect ratio, $\alpha$, and then plot the results. As with all the calculations presented herein, a separation distance of 1.0 nm is utilized. The equation for the curve is written as:

$$D = \frac{9}{4}z_0\alpha^2$$

Figure 13:
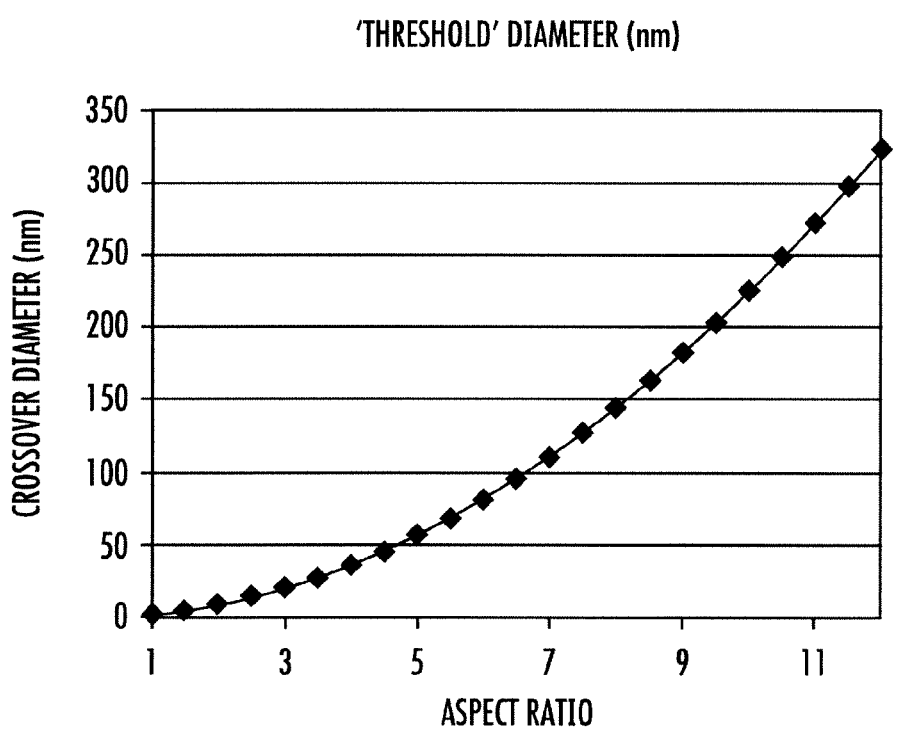
FIGS. 13 and 14 show a graphs comparing crossover diameter to aspect ratio.
Figure 14:
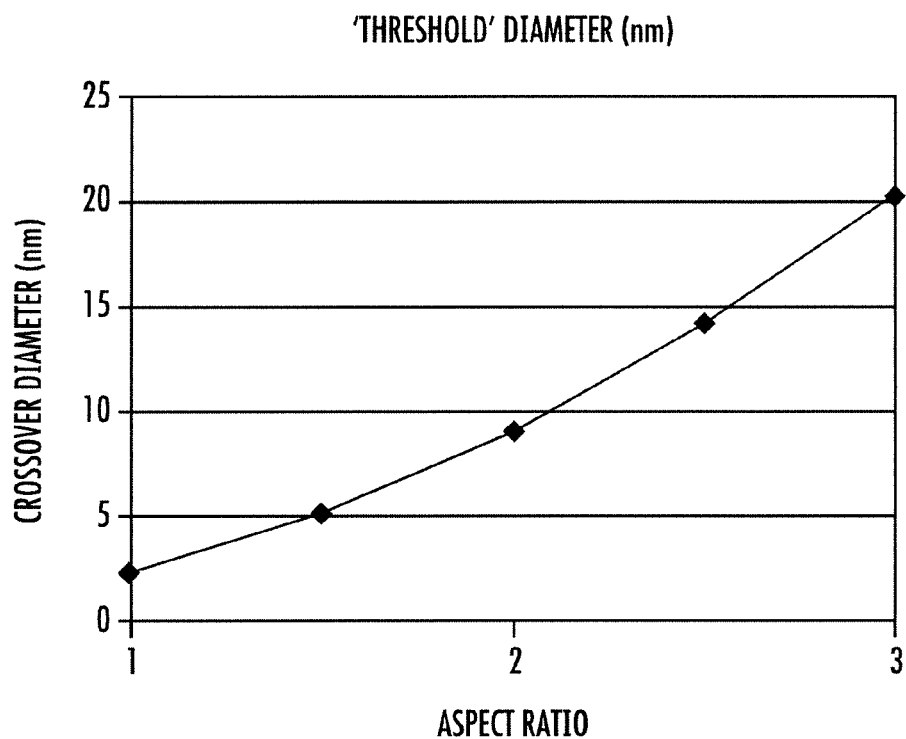

Referring to FIGS. 13 and 14, above the curve the perpendicular orientation is more stable, while the parallel orientation is more stable when beneath the curve. For example, when aspect ratio equals 5, then cylindrical type particles having diameters above about 60 nm prefers the perpendicular orientation. Elongated particles in a parallel or horizontal orientation generally provide a surface with a smooth feel while elongated particles in a perpendicular or vertical orientation generally provide a surface with a rough feel. A perpendicular orientation is absent for sausage shaped particles, which preferably lie parallel to a surface, rather than erect, at all aspect ratios. The threshold diameter feature of cylinder type particles is even true when the aspect ratio is 1, where particles having diameters larger than 2.25 nm prefer the erect state to parallel. At an aspect ratio of 1, cylinders are more like pill boxes while sausages become spheres.

Proof that the surface adhesive force of a cylinder exceeds that of a sausage having equal volume, when in the perpendicular orientation, follows by evaluating the following interaction energy integral:

$$U(z_0) = -\frac{A}{\pi^2}\int\int \frac{d^3x_1 d^3x_2}{X_{12}^6}$$

The equation above consists of two volume integrals—one over the epidermal slab and the second over the volume occupied by the rod shaped particle. The distance between any two points, one inside the rod and the other in the slab (see FIG. 12), is given by $X_{12}$.

Figure 15:
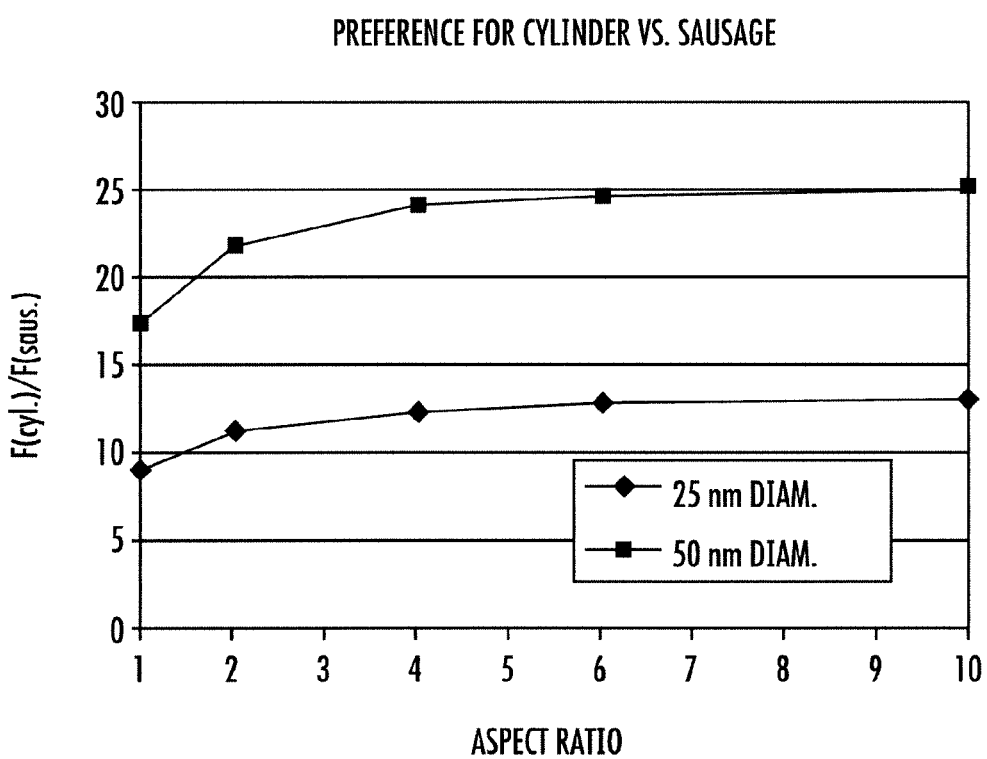
FIG. 15 shows a graph comparing adhesive forces for cylindrically shaped elongated particles vs. sausage shaped cylindrical particles, when each is perpendicular to a surface.

The interaction energy can be plotted as a function of separation distance, $z_0$. The slope of the curve gives the adhesive force. Adhesive forces for the two particle types are compared in FIG. 15 under the constraint that each particle has the same volume as the other. When comparing the two particle types in the erect condition, the cylinder adheres more strongly to the surface than the sausage, regardless of aspect ratio. In the parallel orientation, neither shape is preferred over the other.

Referring again to FIGS. 7 and 8, in certain embodiments of the present disclosure, the orientation of an elongated particle in relation to a surface can be affected by the diameter and aspect ratio of such an elongated particle as well as the application technique of a user. For instance, referring to FIG. 7, elongated particles are oriented both horizontally and vertically in relation to a surface 20 prior to being rubbed by a user, upon which, some of the particles oriented vertically in relation to the surface 20 are moved so as to be oriented horizontally in relation to the surface 20. However, depending on the aspect ratio and diameter of such elongated particles, the elongated particles may re-orient themselves back to being vertical in relation to the surface. Similarly, referring to FIG. 8, elongated particles are oriented horizontally in relation to a surface 20 prior to being rubbed by a user upon which some of the particles are oriented vertically in relation to the surface 20. Again, depending on the aspect ratio and diameter of such elongated particles, the elongated particles may re-orient themselves back to being horizontal in relation to the surface 20. In this manner, the composition can produce a consistent feel, regardless of the method of application to a surface.

In addition to the elongated particles described herein, the composition can optionally include additional particles that can have any desired shape so as to allow for unique sensory attributes in accordance with the present disclosure. Desired particle shapes can include, for example, cubic, polyhedral, spherical or semi-spherical, rounded or semi-rounded, angular, irregular, amorphous, and the like. Such additional particles may be coated or uncoated and can also have varying charges in accordance with the present disclosure. The varying charges preferably affect the orientation of each additional particle in relation to the other additional particles as well as the other elongated particles of the composition.

The elongated particles of the present disclosure generally have a diameter ranging from about 5 nm to about 500 nm. In certain embodiments, the elongated particles have a diameter ranging from about 20 nm to about 100 nm, or about 25 nm to about 65 nm, or about 30 nm to about 60 nm, or about 35 nm to about 55 nm, or about 40 nm to about 50 nm. The elongated particles of the present disclosure generally have an aspect ratio of greater than about 1 and less than or equal to about 10 such that the length of the elongated particle is greater than or equal to the diameter.

A wide variety of materials are suitable for being used for the elongated particles of the present disclosure. Particulate materials useful herein include bismuth oxychloride, iron oxide, mica, surface treated mica, ZnO, ZrO2, silica, silica silyate, colloidal silica, attapulgite, sepiolite, starches (i.e. corn, tapioca, rice), nylon-12, nylon-6, polyethylene, talc, styrene, polystyrene, polypropylene, ethylene/acrylic acid copolymer, acrylates, acrylate copolymers (methylmethacrylate crosspolymer), sericite, titanium dioxide, bismuth oxychloride, iron oxide, aluminum oxide, silicone resin, barium sulfate, calcium carbonate, cellulose acetate, polymethyl methacrylate, polymethylsilsequioxane, boron nitride, lauroyl lysine, and mixtures thereof. These particulates can be coated or uncoated.

The elongated particles contemplated for use with the present disclosure can be produced as would be known in the art utilizing the aspect ratios described herein. Further discussion on production of elongated particles may be found in U.S. Pat. No. 5,597,512, entitled "Method for preparing elongated-shaped silica sol" and Yu, Qingjiang, *Inorganic Chemistry*, 2007, 46, 6204-6210, which are incorporated by reference herein for all purposes.

Particulate materials can be present in the composition of the present disclosure in levels of from about 0.01% to about 100% or from about 0.05% to about 50%, or from about 0.1% to about 20%, by weight of the composition.

In addition to elongated particles, the compositions of the present disclosure can include a carrier. The amount of carrier that can be included in the composition will depend on a variety of factors including the desired characteristics of the composition. The carrier content of the composition can be from about 0%-99.99%. The carrier can include any material within which the elongated particles of the present disclosure can be dispersed. Carriers suitable for use with the present disclosure can include both liquid and solid materials, such as powders and the like. For example, the elongated particles of the present disclosure can be added to known or existing formulations to improve the benefits of such formulations. The carrier can include materials that are hydrophobic, hydrophilic or mixtures thereof.

In one embodiment, a preferable carrier for use in the compositions of the present disclosure can include silicon-based carriers. Silicone-based carriers are organo-silicone-based polymers with repeating siloxane (Si—O) units. Silicone-based carriers of the present disclosure are hydrophobic and exist in a wide range of possible molecular weights. They include linear, cyclic and cross-linked varieties. Silicone oils are generally chemically inert and usually have a high flash point. Due to their low surface tension, silicone oils readily spread and have high surface activity. However, it should be understood that any suitable carrier material can be utilized including Examples of silicon oils suitable for use in the present disclosure include, but are not limited to: cyclomethicones, dimethicones, phenyl-modified silicones, alkyl-modified silicones, silicone resins, and combinations thereof. Other carriers useful in the present disclosure include unsaturated esters or fatty esters, such as ethyl, hexyl stearate or caprylic/capric triglycerides. Additionally, hydrophilic ingredients could be useful in the present disclosure and could include but not be limited to glycols, polyethylene glycols, glycerin, glycerin derivatives, and ethoxylated materials. A table of suitable carriers is presented below, with reference to the trade name and/or distributor and/or INCl. The use of a combination of the above classes of carriers may also be advantageous to properly solubilize all components of the formulation or further changing the spreading and overall aesthetic properties of the formulation.

In certain embodiments of the present disclosure, the refractive index of the elongated particles can be changed to affect the visibility of the elongated particles. The refractive index is the ratio of the velocity of light in a vacuum to its velocity in a substance. It is also the ratio of the sine of the angle of incidence to the sine of the angle of refraction. Light that is not refracted into the material will either be absorbed by the material or reflected off the material's surface.

By changing the charges and aspect ratios of the elongated particles, dyes and colors can be manipulated to adhere or transfer from different parts of a substrate. By way of example only, an image that is adhered and visible on a substrate as a negatively charged dye can align with a positive portion of an elongated particle disclosed herein where it is applied on the substrate. Mixtures of elongated particles with different refractive indices can alter the perception of such images on a substrate. Altering the reflection of light will directly impact the visualization of the state of the surface by the consumer.

In certain embodiments of the present disclosure, the refractive index of the elongated particles can be changed to affect the visibility of the elongated particles on the skin. This could be useful for the consumer in covering and/or disguising the appearance of imperfections, discolorations, and/or wrinkles on the skin. Additionally, the particles could be utilized for altering the visual appearance of wrinkles due to "soft focus" effects.

Additionally, the particles can be utilized on hard surfaces to facilitate gripping and release of objects. Manipulating the refractive index of the surface can also serve to enhance color and shine. Furthermore, visualization of particles can allow for consumer cues to indicate appropriate cleanup of surfaces after use.

The table below also provides the refractive index value for certain of the carriers listed. In certain embodiments, the carrier has a refractive index value of less than about 4.0. In certain embodiments, the carrier has a refractive index value from about less than about 1.6. In certain embodiments, the carrier has a refractive index value from about greater than about 1.2.

Also included in the table is the relative static permittivity or dielectric constant value for each carrier. The relative static permittivity of a material under given conditions is a measure of the extent to which it concentrates electrostatic lines of flux. It is the ratio of the amount of stored electrical energy when a potential is applied, relative to the permittivity of a vacuum. The relative static permittivity is the same as the relative permittivity evaluated for a frequency of zero. In certain embodiments, a relative static permittivity of less than 30 is present. In some embodiments, a relative static permittivity of less than 7 is present.

| Trade Name | INCI | Refractive Index | $\epsilon_r$ |
| --- | --- | --- | --- |
| Finsolv TN | C12-15 Alkyl Benzoate | 1.4837 | 3.8 |
| Elefac I-205 | Octododecyl Neopentanoate | 1.4432 | 3.04 |
| Dub Synersol | Isodecyl Neopentanoate and Diisopropyl Sebacate and Lauryl Lactate | 1.4312 | 4.5 |
| Cetiol LC | Coco-Caprylate/Caprate | 1.4409 | 3.11 |
| Crodamol LGE | Lignoceryl Erucate | 1.4593 | |
| Crodamol ISNP | Isostearyl Neopentanoate | 1.4437 | |
| Floramac 10 | Ethyl Macadamiate | 1.4484 | 3.33 |
| Jojoba Oil Colorless | Jojoba Oil | | 3.1 |
| Ceraphyl 230 | Diisopropyl Adipate | 1.4227 | 5.4 |
| Ceraphyl RMT | Castoryl Maleate | 1.4794 | |
| Ceraphyl 55 | Tridecyl Neopentanoate | 1.4357 | 3.4 |
| Ceraphyl SLK | Isodecyl Neopentanoate | 1.4266 | 3.5 |
| HallStar DOM | Diethylhexyl maleate | 1.4519 | 4.81 |

-continued

| Trade Name | INCI | Refractive Index | $\epsilon_r$ |
|---|---|---|---|
| PureSyn 6 | Hydrogenated Polydecene | 1.4458 | 2.12 |
| Extend 226 | Phenethyl Benzoate | >1.522 | 6.4 |
| Ceraphyl 368 | Ethylhexyl Palmitate | 1.4441 | 3.08 |
| Crodaderm S | Sucrose Polysoyate Sucrose Polybehenate | >1.522 | 3.02 |
| Ceraphyl 375 | Isostearyl Neopentanoate | 1.4414 | 3.13 |
| Ceraphyl 31 | Lauryl Acetate | 1.4433 | 5.51 |
| Lexol IPL | Isopropyl Laurate | 1.4252 | 3.4 |
| Crodamol STS | PPG-3 Benzyl Ether Myristate | 1.4691 | 4.5 |
| Spectrasolv 16 | DIETHYLHEXYL MALATE | 1.4501 | 5.9 |
| Permethyl 102A | Isoeicosane | 1.4492 | 2.11 |
| Crodamol PMP | Cetearyl Ethylhexanoate | 1.4365 | 4 |
| Cetiol CC | Di-N-Octyl Carbonate | 1.4341 | 2.41 |
| Cetiol B | Dibutyl Adipate | 1.4304 | 5.1 |
| Hydrolite-5 | Pentylene Glycol | 1.4387 | 18.41 |
| Symdiol 68 | 1,2 Hexanediol/1,2 Octanediol | 1.4469 | 13.13 |
| LexGuard 0 | 1,2 Octanediol | 1.4383 | |
| Escalol 567 | Benzophenone-3 | >1.522 | 13 |
| Escalol 597 | Octocrylene | >1.522 | 11.08 |
| | 1,3 Butylene Glycol | | 28.8 |
| Ethox 4100 | Polyethylene Glycol-7 Methyl Ether | | 13.1 |
| MPDiol Glycol | Methylpropanediol | | 28.8 |
| DC 200 Fluid (100/350 cst) | Dimethicone | >1.522 | |
| DC 245 | Cyclomethicone | >1.522 | |
| DC 1503 | Dimethicanol/Dimethicon | 1.3985 | |
| Silsoft 440 | PEG/PPG-20/23 Dimethicane | 1.4468 | 5.6 |
| HallBrite BHB | Butyloctyl Salicylate | 1.4921 | 5.5 |
| Spectrasolv 10 | Diisoamyl Malate | | 7.42 |
| Dowanol DB | Diethylene Glycol Monobutyl Ether | 1.4305 | 10.59 |
| Educol-421 | Ethoxydiglycol | 1.4265 | 13.69 |
| BG Monopropionate | Butylene Glycol Monopropionate | 1.4266 | 11.72 |
| | 1,2-Hexanediol | 1.4422 | 15.1 |
| Spectrasolv DMDA | N,N Dimethyldesamide | 1.4529 | 12.43 |

The compositions of the present disclosure may also contain one or more additional components. For instance, certain components can be added to the composition that are suitable for contact with human keratinous tissue. Hence, such additional components do not have undue toxicity, incompatibility, instability, allergic response, and the like within the scope of sound medical judgment. However, the compositions of the present disclosure are not limited to use on skin surfaces as they have equal utility as compositions for use on other surfaces as well. For example, the surface can include an animate surface such as skin, hair, mucosal, teeth, oral surfaces and other surfaces of the body, human or otherwise, including pets. In addition, other inanimate surfaces including countertops, glass, and the like are contemplated for use in connection with the present disclosure.

The CTFA Cosmetic Ingredient Handbook, Second Edition (1992) describes a wide variety of nonlimiting cosmetic and pharmaceutical ingredients commonly used in the skin care industry, which are suitable for use in the compositions of the present disclosure. Examples of these ingredient classes include: abrasives, absorbents, aesthetic components such as fragrances, pigments, colorings/colorants, essential oils, skin sensates, astringents (clove oil, menthol, camphor, eucalyptus oil, eugenol, menthyl lactate, witch hazel distillate), anti-acne agents, anti-caking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, opacifying agents, pH adjusters, propellants; reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and panthenol derivatives, aloe vera, pantothenic acid, pantothenic acid derivatives, allantoin, bisabolol, and dipotassium glycyrrhizinate), skin treating agents, sunscreens, thickeners, and vitamins and derivatives thereof.

Peptides, including but not limited to, di-, tri-, tetra-, and pentapeptides and derivatives thereof, may be included in the compositions of the present disclosure in amounts that are safe and effective. As used herein, "peptides" refers to both the naturally occurring peptides and synthesized peptides. Also useful herein are naturally occurring and commercially available compositions that contain peptides.

When included in the present compositions, peptides can be present in amounts of from about $1\times10^{-6}\%$ to about 10%, or from about $1\times10^{-6}\%$ to about 0.1%, or from about $1\times10^{-6}\%$ to about 0.01%, by weight of the composition.

In certain embodiments of the present disclosure, the charged elongated particles of the present disclosure would also have the ability to be carriers for above-described additional components and act as delivery vehicles. For example, a positively charged molecule like a peptide could be delivered from elongated particles as described herein having split charges. The peptide could penetrate into the skin as the positive charge of the peptide is attracted to the negatively charged surface of the skin.

In any embodiment of the present disclosure, however, the active ingredients useful herein can be categorized by the benefit they provide or by their postulated mode of action. However, it is to be understood that the active ingredients useful herein can in some instances provide more than one benefit or operate via more than one mode of action. Therefore, classifications herein are made for the sake of convenience and are not intended to limit the active to that particular application or applications listed.

Once formed, in some embodiments the composition described above can be applied to substrates, wipes, cotton balls, or any other viable form. For example, a paper product may be formed from any papermaking process known in the art. For example, a papermaking process of the present disclosure can utilize creping, embossing, wet-pressing, double creping, calendering, as well as other known steps in forming the paper web. One particular embodiment of the present disclosure utilizes a non-compressive drying technique, such as uncreped through-drying, to form the paper product. In some instances, an uncreped through-dried paper product may have good absorbency and wet-resiliency characteristics. Some examples of uncreped through-drying techniques are disclosed in U.S. Pat. No. 5,048,589; U.S. Pat. No. 5,399,412; U.S. Pat. No. 5,510,001; U.S. Pat. No. 5,591,309; and U.S. Pat. No. 6,017,417, which are incorporated herein in their entirety by reference thereto for all purposes.

For example, uncreped through-drying generally involves the steps of: (1) forming a furnish of cellulosic fibers, water, and optionally, other additives, such as debonders and wet-strength agents; (2) depositing the furnish on a traveling foraminous belt, thereby forming a fibrous web on top of the traveling foraminous belt; (3) subjecting the fibrous web to through-drying to remove the water from the fibrous web; and (4) removing the dried fibrous web from the traveling foraminous belt.

In some embodiments, once the paper web is dried, the composition described above can then be applied. In general, the composition of the present disclosure can be applied to the paper product using a variety of methods. For instance, in one embodiment, the composition can be applied to the surface of the paper product using rotogravure printing, either direct or indirect (offset). Rotogravure printing can sometimes offer better control of the distribution and transfer rate of the composition onto the paper product. In addition, other application methods, such as flexographic printing, spraying (e.g., WEKO), hot melt adhesive spraying (e.g., Nordson), blade, saturant, coating, droplet throw, and foam applications, can be used.

Further, the composition can be applied to one or both outer surfaces of the product after the product has been dried. When utilizing a multi-ply paper product, the composition can be applied after the plies are brought together or prior to bringing the plies together. The individual plies can be layered or blended (homogeneous), creped or uncreped, through-dried or wet-pressed. In one embodiment, for example, the paper product is an uncreped through-dried paper product.

The add-on level of the composition can generally vary depending on the desired effect of the composition on the product attributes and the specific composition. For example, the add-on level of the composition can be from about 200% to about 500% by weight of the paper web, and in some embodiments, from about 250% to about 350% by weight of the paper web.

In addition, the compositions of the present disclosure may be formulated as is known in the art for direct application to a surface. Forms chiefly conditioned for surface application can take any form including, for example, hydrous, anhydrous, emulsions, aerosol formulations (e.g., sprays or foams), or any other viable formulation type. In addition, the present compositions can be provided in any suitable dispenser as would be known in the art such as bottles, tubes, jars, sprays or any other viable form.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure may be practiced by those of ordinary skill in the art, without departing from the spirit and scope of the present disclosure, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the disclosure so further described in such appended claims.

What is claimed:

1. A method of applying a particulate material composition to a surface, the method including the steps of:
applying a particulate material composition to a surface, the particulate material composition comprising a carrier material and a plurality of elongated particles of cylindrical symmetry having a diameter of from about 5 nm to about 500 nm, the plurality of elongated particles further having a length that is greater than the diameter with such elongated particles having a diameter that is within 10% of $$\frac{9}{4}z_0\alpha^2,$$

wherein the separation distance, $z_0$, is about 1 nm and the aspect ratio, $\alpha$, is greater than 1, the diameter and the aspect ratio affecting the orientation of such elongated particles in relation to a surface on which the particulate material composition is applied, wherein as a result of applying the particulate material composition to the surface some of the elongated particles are oriented perpendicular to the surface on which the particulate material composition is applied and some of the elongated particles are oriented horizontal to the surface on which the particulate material composition is applied; and
wherein some of the elongated particles that are oriented perpendicular to the surface re-orient themselves so as to be oriented horizontal to the surface or some of the elongated cylindrical particles that are oriented horizontal to the surface re-orient themselves so as to be oriented vertical to the surface.

2. The method of claim 1, wherein the elongated particles have an aspect ratio of at least about 3.

3. The method of claim 1, wherein the elongated particles have an aspect ratio of at least about 5.

4. The method of claim 1, wherein the elongated particles have an aspect ratio of at least about 10.

5. The method of claim 1, wherein the surface comprises an inanimate surface.

6. The method of claim 1, wherein the surface comprises an animate surface.

7. The method of claim 1, wherein the particulate material composition is provided in a dispenser.

8. The method of claim 5, wherein the particulate material composition is applied by hand to the inanimate surface.

9. The method of claim 6, wherein the particulate material composition is applied by hand to the animate surface.

10. The method of claim 1, wherein a portion of the elongated particles have a tendency to be oriented perpendicular to the surface on which the particulate material composition is applied.

11. The method of claim 1, wherein a portion of the elongated particles have a tendency to be oriented horizontal to the surface on which the particulate material composition is applied.

* * * * *